United States Patent [19]

Taeusch et al.

[11] Patent Number: 4,882,422

[45] Date of Patent: Nov. 21, 1989

[54] PULMONARY SURFACTANT PROTEINS

[75] Inventors: H. William Taeusch, Redondo Beach, Calif.; Kenneth A. Jacobs, Newton, Mass.; D. Randall Steinbrink, Melrose, Mass.; Joanna Floros; David S. Phelps, both of West Roxbury, Mass.; Edward F. Fritsch, Concord, Mass.

[73] Assignee: Genetics Institute, Inc., Cambridge, Mass.

[21] Appl. No.: 100,372

[22] Filed: Sep. 24, 1987

Related U.S. Application Data

[63] Continuation-in-part of Ser. No. 791,120, Sep. 26, 1985, abandoned, and a continuation-in-part of Ser. No. 897,183, Sep. 26, 1985, abandoned.

[51] Int. Cl.$^4$ .................... C07K 13/00; A61K 37/02
[52] U.S. Cl. .................................. 530/350; 530/808; 435/68; 435/70; 935/60
[58] Field of Search ...................... 530/300, 350, 808; 435/68, 70; 935/60

[56] References Cited

U.S. PATENT DOCUMENTS 4,659,805  4/1987  Schilling, Jr. et al. ............. 530/350

OTHER PUBLICATIONS

Weinberg et al, "Isolation and Characterization of Humawn Apolipoprotein A-IV from Lipoprotein-Depleted Serum", J. Lipid Res., vol. 24, 1983, pp. 52-59.

Utermann et al, "Apolipoprotein A-IV: A Protein Occurring in Human Mesenteric Lymph Chylomicrons and Free in Plasma", Eur. J. Biochem. 99, 333-343 (1979).

Weisgraber et al, "Isolation and Characterization of an Apoprotein from the d>1.006 Lipoproteins of Human and Canine Lymph Homologous with the Rat A-IV Apoprotein", Biochem Biophys Res Comm, vol. 85, No. 1, 1978, pp. 287-292.

Green et al, "Human Apolipoprotein A-IV-Intestinal Origin and Distribution in Plasma", J. Clin. Invest., vol. 65, Apr. 1980, 911-919.

Beisiegel et al, "An Apolipoprotein Homolog of Rat Apolipoprotein A-IV in Human Plasma", Eur. J. Biochem, 93, 601-608 (1979).

Floros et al, "Biosynthesis and in Vitro Translation of the Major Surfactant-Associated Protein from Human Lung", J. of Biol Chem., vol. 260, No. 1, 495-500, Jan. 10, 1985.

Hawgood et al, "Effects of a Surfactant-Assocaited Protein and Calcium Ion on the Structure and Surface Activity of Lung Surfactant Lipids", Biochemistry, 1984, 24, 184-190.

Bhattacharyya et al, "Isolation and Characterization of Two Hydroxyproline-Containing Glycoproteins from Normal Animal Lung Lavage and Lamellar Bodies", J. Clin Invest., vol. 55, May 1975, 914-920.

Primary Examiner—John Kight
Assistant Examiner—Nathan M. Nutter
Attorney, Agent, or Firm—David L. Berstein; Bruce M. Eisen

[57] ABSTRACT

This invention relates to novel proteins useful for enhancing pulmonary surfactant activity, methods for obtaining said proteins and compositions containing one or more of the proteins. The proteins of this invention include the following:

1. A protein characterized by a molecular weight of about 35 kd and by being encoded for by the DNA sequence depicted in Table 1.
2. A protein characterized by a molecular weight of about 35 kd and by being encoded for by the DNA sequence depicted in Table 2.
3. A protein encoded for by a portion of the DNA sequence depicted in Table 6 and characterized by a molecular weight of about 5.5–9 kd; and
4. A protein characterized by a molecular weight of about 5.5–9 kd and an amino acid composition as set forth in Table 4.

1 Claim, No Drawings

PULMONARY SURFACTANT PROTEINS

This application is a continuation-in-part of U.S. Ser. Nos. 791,120 and 897,183, filed Sept. 26, 1985 and Aug. 15, 1986, respectively and both now abandoned, the contents of which are hereby incorporated by reference. This application further claims the priority benefit under 35 USC §119 of PCT/US86/02034, filed Sept. 26, 1986.

FIELD OF THE INVENTION

This invention relates to proteins isolated from human lung lavage, methods for obtaining said proteins and uses thereof.

BACKGROUND OF THE INVENTION

Throughout this application various publications are referenced. Full citations for these publications may be found at the end of the specification. The disclosure of these publications are hereby incorporated by reference in order to more fully describe the state of the art to which this invention pertains.

Hyaline Membrane Disease (HMD) and Respiratory Distress Syndrome (RDS) are synonymous terms denoting the clinical condition of pulmonary dysfunction in premature infants. The disease is attributable to the absence of surface active material (surfactant) which lines the air-alveolar interface in the lung and prevents collapse of the alveoli during respiration. Current therapy is predominantly supportive. However, recent clinical trials indicate that one promising therapy is the instillation of bovine-derived surfactant into the lungs of the neonate.

Surface tension in the alveoli of the lung is lowered by a lipoprotein complex called pulmonary surfactant. This complex consists of phospholipid and 5-10% protein (King, 1982). The protein fraction of the surfactant is composed of nonserum and serum proteins. The major surfactant associated protein is reportedly a 35,000 dalton nonserum, sialoglycoprotein (Shelly et al., 1982; Bhattacharyya et al, 1975; Sueishin and Benson 1981; King et al, 1973, Katyal & Singh, 1981). This protein reportedly seems to be important for the normal function of the pulmonary surfactant (King et. al., 1983; Hawgood et.al., 1985). It is present in reduced amounts in amniotic fluid samples taken shortly before the birth of infants who subsequently develop respiratory distress syndrome (Katyal and Singh, 1984; Shelly et al., 1982; King et al., 1975). Recently the biosynthesis of a 35,000 dalton protein in normal human lung tissue was studied and in an invitro translation reaction, proteins of 29 and 31 kDa were identified as the primary translation products (Floros et al., 1985). A 35 kDa protein also accumulates in the lungs of patients with alveolar proteinosis (Battacharyya and Lynn, 1978, Battacharyya and Lynn, 1980a). This protein has the same electrophoretic mobility, immunological determinants and peptide mapping as the 35 kDa protein from normal human bronchoalveolar lavage material (Phelps et al., 1984; Whitsett et al., 1985).

In addition to the above mentioned proteins, the presence in rat lungs of a number of lower molecular weight surfactant-associated proteins has recently been reported. See D. L. Wang, A. Chandler and A. B. Fisher, Fed. Proc. 44(4): 1024 (1985), Abstract No. 3587 (ca. 9000 dalton rat protein) and S. Katyal and G. Singh, Fed. Proc. 44(6): 1890 (1985), Abstract No. 8639 (10,000–12,000 dalton rat protein).

Finally, a Feb. 6, 1985 press release from California Biotechnology Inc. reports the cloning and "detailed manipulation" of "the gene encoding human lung surfactant protein." However, the press release does not characterize that protein or describe the "detailed manipulations." Two other reports of possible surfactant-related proteins have also been published recently, namely, J. A. Whitsett et al., 1986, Pediatr. Res. 20:460 and A. Takahashi et al., 1986, The present invention relates to a new group of proteins recovered and purified from lung lavage of patients with alveolar proteinosis, methods for obtaining the proteins, corresponding recombinant proteins, antibodies to the proteins for use in diagnostic products, compositions containing the novel proteins, and methods for using the compositions, e.g. in the treatment of infants afflicted with conditions such as Respiratory Distress Syndrome (RDS), as a drug delivery vehicle in the administration of other therapeutic materials to the lungs or other organs and in the treatment of adult RDS, which can occur during cardiopulmonary operations or in other situations when the lungs are filled with fluid and natural pulmonary surfactant production and/or function ceases. While it is possible that one or more of the proteins described hereinafter is similar or identical to proteins discussed in the abovementioned papers, the exact relationship of the protein of this invention to prior proteins cannot at present be confirmed given the inadequacies of the prior disclosures with respect to amino acid or nucleotide sequence data, surfactant activity of prior proteins and the like.

SUMMARY OF THE INVENTION

This invention relates to novel proteins useful for enhancing pulmonary surfactant activity, methods for obtaining said proteins and compositions containing one or more of the proteins. The proteins of this invention include the following:

1. A protein characterized by a molecular weight of about 35 kd and by being encoded for by the DNA sequence depicted in Table 1.

2. A protein characterized by a molecular weight of

TABLE 1

DNA and Protein Sequence of 35K PSP Clone 1A

| | | | | | | | | | | | |
|---|---|---|---|---|---|---|---|---|---|---|---|
| | | | | | | | | | GAA | TTCCGCAGAG | CTGGAGGCTC |
| | | | | | | | | | | | ATG MET |
| TGTGTGTGG | | TCGCTGATTT | | CTTGGAGCCT | | GAAAAGAAGG | | AGCAGCGACT | | GGACCCAGAG | ACCAAGCAC |
| | 290 | | 300 | | 310 | | 320 | | 330 | 340 | |
| TGG Trp | CTG Leu | TGC Cys | CCT Pro | CTG Leu | GCC Ala | ACC Thr | CTC Leu | ATC Ile | TTG Leu | ATG MET | GCA Ala | GCC Ala | TCT Ser | GCT Ala | GCG Ala |
| | | | | | | 372 | | | | | | 387 | | | |
| TGC Cys | GAA Glu | GTG Val | AAG Lys | GAC Asp | GTT Val | TGT Cys | AGC Ser | GGT Gly | CCT Pro | GGT Gly | ATC Ile | CCC Pro | GGC Gly | CCT Pro | GGA Gly |
| 402 | | | | | 417 | | | 432 | | | 447 | | | | |
| TCC Ser | CAC His | GGC Gly | CCC Pro | CTG Leu | GGT Gly | AGG Arg | AGA Arg | GGT Gly | GAT Asp | ACA Thr | GGA Gly | AAA Lys | GGC Gly | CCT Pro | GGA Gly |
| 462 | | | | | 477 | | | 492 | | | 507 | | | | |
| CCT Pro | CCA Pro | CCC Pro | GGA Gly | CCA Pro | CCT Pro | GAC Asp | CAA Gln | AGA Arg | ACA Thr | CCA Pro | CCT Pro | GAG Glu | GGA Gly | GAC Asp | GGT Gly |
| | | 522 | | | | 537 | | | | 552 | | | | | |
| GGG Gly | CCA Pro | GGA Gly | ATG MET | GGT Gly | GGG Gly | GAA Glu | AAG Lys | GAA Glu | CAT His | CGT Arg | CCT Pro | AAG Lys | GGG Gly | GAG Glu | AAT Asn |
| | 567 | | | | 582 | | | 597 | | | 612 | | | | |
| GGC Gly | CTG Leu | CCT Pro | GGA Gly | CCT Pro | GGT Gly | CAT His | CAA Gln | GGA Gly | CTA Leu | ACA Thr | GGA Gly | GAG Glu | GGG Gly | GAG Glu | CCT Pro |
| | | | | | | | | | | 627 | | | | | |
| GGC Gly | CTC Leu | AGA Arg | GAC Asp | TTC Phe | ATG MET | GGG Gly | CAT His | CTC Leu | CAA Gln | ACA Thr | ATC Ile | CCT Pro | GAT Asp | GGG Gly | AAT Asn |
| 672 | | | | | 687 | | | 702 | | | 717 | | | | |
| ACA Thr | GAG Glu | CTC Leu | ATA Ile | ATG MET | AGA Arg | ACA Thr | ATT Ile | GTC Val | GCA Ala | TTC Phe | AAT Asn | AAG Lys | CTC Leu | ATT Ile | CCT Pro |
| | | | | | | 732 | | | | 747 | | | | | |
| CAG Gln | GGC Gly | TTT Phe | GAT Asp | GCC Ala | ATT Ile | GAG Glu | GAG Glu | GTC Val | GCC Ala | GCA Ala | GAG Glu | GAG Glu | GGG Gly | CAG Gln | AGT Ser |
| 762 | | | | | 777 | | | | | | | | | | |
| ATC Ile | ACT Thr | AGG Arg | AAT Asn | CCA Pro | GAG Glu | ATC Ile | GAG Glu | GCA Ala | GCC Ala | GCA Ala | AAT Asn | GGC Gly | CGC Arg | ATT Ile | CCT Pro |
| | 807 | | | | | | | 822 | | | | | | | |
| GTC Val | CCA Pro | GCC Ala | AAT Asn | CCA Pro | GAA Glu | GAG Glu | GAG Glu | GCA Ala | GCA Ala | GCC Ala | AGC Ser | TTC Phe | GTG Val | AAG Lys | TAC Tyr |
| | 837 | | | | 852 | | | 867 | | | 882 | | | | |
| AAC Asn | ACA Thr | AGG Arg | TAT Tyr | TAT Tyr | GTA Val | GAG Glu | GAG Glu | GCA Ala | CCC Pro | TTC Phe | AGC Ser | GGG Gly | AAG Lys | GAC Asp | CGC Arg |
| | | 897 | | | | 912 | | | | 927 | | | | | |
| AAC Asn | TCA Ser | GCC Ala | GGG Gly | TAT Tyr | GGC Gly | ACT Thr | GAG Glu | GCA Ala | CCC Pro | CCT Pro | GGA Gly | GAC Asp | GAC Asp | TTC Phe | TAC Tyr |
| 942 | | 957 | | | 972 | | | 987 | | | | | | | |
| TAC | GAT | CCT | GTA | AAC | AAC | TGG | TAC | CAG | CGG | CGA | CCT | | | | GCA |

TABLE 1-continued
DNA and Protein Sequence of 35K PSP Clone 1A

| Tyr | Ser | Asp | Gly | Thr | Pro | Val | Asn | Tyr | Thr | Asn | Trp | Tyr | Arg | Gly | Glu | Pro | Ala |
|---|---|---|---|---|---|---|---|---|---|---|---|---|---|---|---|---|---|
| | | 1002 | | | | | | 1017 | | | | 1032 | | | | | 1047 |
| GGT | CGG | GGA | AAA | GAG | CAG | TGT | GTG | GAG | ATG | TAC | ACA | GAT | GGG | CAG | TGG | AAT | GAC |
| Gly | Arg | Gly | Lys | Glu | Gln | Cys | Val | Glu | Met | Tyr | Thr | Asp | Gly | Gln | Trp | Asn | Asp |
| AGG | AAC | TGC | CTG | 1062 TAC | TCC | CGA | CTG | 1077 ATC | GAG | TGT | TTC | TGA | | | 1099 GAGGCATTTA | 1109 GGCCATGGGA | |
| Arg | Asn | Cys | Leu | Tyr | Ser | Arg | Leu | Ile | Glu | Cys | Phe | *** | | | | | |

1119 CAGGGAGGAT  1129 CCTGTCTGGC  1139 CTTCAGTTTC  1149 CATCCCCAGG  1159 ATCCACTTGG  1169 TCTGTGAGAT  1179 GCTAGAACTC

1189 CCTTTCAACAGAATTC about 35 kd and by being encoded for by the DNA sequence depicted in Table 2.

3. A protein encoded for by the DNA sequence of Table 6 or by a DNA sequence capable of hybridizing thereto and characterized by a molecular weight of about 5.59kd; and 4. A protein characterized by a molecular weight of about 6 kd and an amino acid composition as set forth in Table 4.

DETAILED DESCRIPTION OF THE INVENTION

The proteins of this invention were obtained by subjecting pulmonary lavage material from an alveolar proteinosis patient to a combination of separation techniques followed by chromatographic purification. More specifically, the lavage material was centrifuged, and the protein-containing pellet so obtained was washed with buffer and extracted with a solvent such as 1-butanol to remove lipids and lipidassociated proteins. The butanol extract was set aside and treated as described below. The 1-butanol-insoluble material was then washed, redissolved in buffer and purified chromatographically. Two proteins were thus obtained which are characterized by a molecular weight of about 35 kd. One of the 35 kd proteins is encoded for by the DNA sequence depicted in Table 1; the second 35 kd protein is encoded for by the DNA sequence depicted in Table 2. Butanol-soluble proteins were obtained by cryoprecipitation. More specifically, storage of the 1-butanol extract at −20° C. yielded a precipitate which was purified chromatographically to yield a protein characterized by an apparent molecular weight of about 6 kd (as determined by SDS-PAGE) and the observed amino acid composition set forth in Table 3. A second 6 kd (as determined by SDS-PAGE) protein was obtained by concentrating the supernatant to dryness and purifying the residue chromatographically. The observed amino acid

TABLE 2

DNA and Protein Sequence of 35K PSP Clone 6A

| | | | | | | | | | | |
|---|---|---|---|---|---|---|---|---|---|---|
| AGAGCAGCGA | 80 | CTGGACCCAG | 90 | GAATTCCGGA | GACCCAAGCA | GCTGGAGGCT | CGTGTGTCO | GTCCCTGAGT | TTCTTGGAGC | CTGAAAAGAA |
| | | | | AGCC | ATG MET | TGG Trp | CTG Leu | TGC Cys | 109 CCT Pro | 124 CTC Leu |
| TTG Leu | ATG MET | GCA Ala | | | GCG Ala | 154 TGC Cys | GAA Glu | GTG Val | AAG Lys | ATC Ile |
| 184 CCT Pro | GGT Gly | ATC Ile | 139 GCC Ala | TCT Ser | GGA Gly | CCT Pro | GCC Ala | 169 GTT Val | CTG Leu | AGC Ser |
| GAT Asp | GGT Gly | 244 CTC Leu | CCC Pro | GGC Gly | GGA Gly | TCC Ser | 214 GCC Gly | CTG Leu | GGC Gly | GGA Gly |
| ATG MET | CCA Pro | TGT Cys | AAA Lys | GGA Gly | GAT Asp | CAC His | GGG Gly | CCC Pro | 229 GAC Asp | AGA Arg |
| 184 CCT Pro | GGT Gly | AGG Arg | 304 CCT Pro | AAG Lys | AAT Asn | CCA Pro | GGG Gly | CCT Pro | CCT Pro | AGG Arg |
| GAT Asp | CTA Leu | AGG Arg | GAG Glu | GAG Glu | 364 GAG Glu | CCA Pro | 274 ATG MET | CCA Pro | ATC Ile | 289 GAA Glu |
| ATG MET | CAG Gln | GGA Gly | GAA Lys | GCC Ala | CAA Gln | 319 CTG Leu | CCT Pro | AGG Arg | GGA Gly | GGA Gly |
| GAG Glu | TGT Cys | 349 TGT Cys | GAG Glu | GGC Ala | AAT Asn | GCT Ala | AGG Arg | 379 GCC Gly | CCC Pro | CCG Pro |
| CAT His | GAT Asp | ACA Thr | AGC Ser | AGT Ser | GGG Gly | GGC Gly | CAC His | GAC Asp | 334 GGT Gly | GCT Ala |
| CAT His | CTA Leu | AGG Arg | 409 GAG Glu | 454 AAT Asn | CAG Gln | CTC Leu | AGG Arg | GCC Ala | ATC Ile | CTG Leu |
| 454 CAG Gln | ACA Thr | GGA Gly | GGC Ala | CAG Gln | ATC Ile | ACT Thr | TTT Phe | AGA Arg | CAT His | AAG Lys |
| GTC Val | TTC Phe | AGC Ser | TTC Phe | AGT Ser | ATC Ile | GGC Gly | TCC Ser | ATG MET | GGG Gly | 499 GGA Gly |
| GCC Ala | AGA Arg | GGC Gly | GGA Gly | GCT Ala | CAG Gln | GAG Glu | TTT Phe | ACG Thr | ATC Ile | GTA Val |
| GCC Ala | AGA Arg | 514 TCC Ser | 574 GGC Gly | AGT Ser | CAG Gln | 589 CCA Pro | AGG Arg | ATG MET | CAT His | CAG Gln |
| ATT Ile | GCA Ala | GCA Ala | GTG Val | AAT Asn | ATT Ile | ACA Thr | 544 GCC Ala | ATG MET | ATT Ile | GTA Val |
| ATT Ile | 619 GCA Ala | AGC Ser | TTC Phe | TAC Tyr | AAG Lys | ACA Thr | CCA Pro | GAG Glu | GAT Asp | 499 GGA Gly |
| GCC Ala | AGA Arg | GGC Gly | AGC Ser | TAC Tyr | AAG Lys | ACT Thr | TAT Tyr | ATA Ile | GAT Asp | CAG Gln |
| ATT Ile | AGA Arg | AGC Ser | 679 CCT Pro | CGC Arg | TTC Phe | TCA Ser | TAT Tyr | GAG Glu | AAT Asn | AAG Lys |
| 454 CAG Gln | AAG Lys | 634 AAG Lys | TTC Phe | GAC Asp | 649 GCC Ala | AGG Arg | GAC Asp | GAG Glu | GCC Ala | 559 TGT Cys |
| GCC Ala | GCA Ala | AGC Ser | TTC Phe | CGC Arg | TTC Phe | GGC Gly | TAC Tyr | GAG Glu | CTG Leu | GCC Ala |
| GTC Val | ACA Thr | GCA Ala | AAA Lys | TAC Tyr | AAG Lys | ACA Thr | CCA Pro | GTA Val | AAC Asn | GAG Glu |
| GCC Ala | CCC Pro | GCC Ala | GCC Ala | AAT Asn | ATC Ile | ACT Thr | CCA Pro | ATC Ile | CTG Leu | GCA Ala |
| ATT Ile | GCA Ala | GCA Ala | TTC Phe | TAC Tyr | GTC Val | CAG Gln | TAT Tyr | GAG Glu | GCA Ala | GAG Glu |
| ATT Ile | AGA Arg | TTC Phe | GGG Gly | AAT Asn | CAG Gln | CAG Gln | TTT Phe | ATT Ile | GAG Glu | GAG Glu |
| GCC Ala | AGA Arg | AGC Ser | TTC Phe | CGC Arg | TTC Phe | GCA Ala | CCT Pro | ACG Thr | 664 ACT Thr | GAG Glu |
| ATT Ile | AGA Arg | AGC Ser | 679 CCT Pro | CGC Arg | TTC Phe | TCA Ser | TAT Tyr | GAG Glu | AAT Asn | AAG Lys |
| GTC Val | ACA Thr | AGC Ser | 679 CCT Pro | CGC Arg | TTC Phe | GGC Gly | TAC Tyr | GAG Glu | 664 ACT Thr | GAG Glu |
| GCC Ala | CCC Pro | AGC Ser | TTC Phe | TAC Tyr | GAC Asp | TCA Ser | TAT Tyr | CCA Pro | TAC Tyr | ACC Thr |
| GGT Gly | CCC Pro | 679 CCT Pro | TTC Phe | TAC Tyr | GAC Asp | ACC Thr | TAT Tyr | 709 CCT Pro | TAC Tyr | GTA Val |
| ATT Ile | GCA Ala | AGC Ser | 679 CCT Pro | CGC Arg | TTC Phe | TCA Ser | TAT Tyr | GAG Glu | AAC Asn | ACC Thr |
| 724 AAC Asn | | | 694 TAC Tyr | | | | | | 769 GTG Val | |
| 739 GAG | TAC | CGA | GGG | CCC | 754 GGA | CGG | GCA | CAG | | |
| | TGG | TAC | CGA | | | | | | | |

TABLE 2-continued

DNA and Protein Sequence of 35K PSP Clone 6A

| Asn | Trp | Tyr | Arg | Gly | Glu | Pro | Ala | Gly | Arg | Gly | Lys | Glu | Gln | Cys | Val | Glu | MET |
|---|---|---|---|---|---|---|---|---|---|---|---|---|---|---|---|---|---|
| | | 784 | | | | | 799 | | | | | 814 | | | | | 829 |
| TAC | ACA | GAT | GGG | CAG | TGG | AAT | GAC | AGG | AAC | TGC | CTG | TAC | TCC | CGA | CTG | ACC | ATC |
| Tyr | Thr | Asp | Gly | Gln | Trp | Asn | Asp | Arg | Asn | Cys | Leu | Tyr | Ser | Arg | Leu | Thr | Ile |
| TGT | GAG | TTC | TGA | | | | | | | | | | | | | | |
| Cys | Glu | Phe | | | | | | | | | | | | | | | |

851 GAGGCATTTA  861 GGCCATGGGA  871 CAGGGAGGAC  881 GCTCTCTGGC  891 CTTCGGCCTC
901 CATCCTGAGG  911 CTCCACTTGG  921 TCTGTGAGAT  931 GCTAGAACTC  941 CCTTTCAACA

| | TABLE 3 | TABLE 4 |
|---|---|---|
| Asp/Asn | 3.06 | 2.7 |
| Thr | 1.18 | 2.0 |
| Ser | 2.55 | 2.1 |
| Glu/Gln | 5.97 | 1.6 |
| Pro | 7.64 | 6.3 |
| Gly | 7.38 | 22.9 |
| Ala | 9.13 | 3.3 |

-continued

| | TABLE 3 | TABLE 4 |
|---|---|---|
| Cys | 9.14 | 0.95 |
| Val | 10.13 | 5.5 |
| Met | 3.46 | 3.4 |
| Ile | 6.46 | 4.8 |
| Leu | 16.23 | 17.3 |
| Tyr | 2.31 | 3.3 |
| Phe | 1.55 | 6.3 |
| His | .34 | 2.9 |
| Lys | 1.62 | 3.6 |
| Arg | 7.88 | 1.94 |

(calculated based on MW = 10,000 daltons; ave residue MW = 110)

TABLE 6
DNA and Corresponding Protein Sequence of 6K Clone

| Pos | | | | | | | | | | | |
|---|---|---|---|---|---|---|---|---|---|---|---|
| 10 | GAATTCCGGT | GCC | ATG Met | GCT Ala | GAG Glu | TCA Ser | CAC His (28) | CTG Leu | CTG Leu | CTG Leu | CTG Leu (43) |
| 58 | CCC Pro | TGT Cys | GGC Gly | CCA Pro | GGC Gly | ACT Thr | GCT Ala (73) | TGG Trp | GCC Ala | TCC Ser | TTG Leu (88) |
| 103 | TTG Leu | GCC Ala | TGC Cys | | | | | | | | |
| 118 | GCC Ala | GGC Gly | GGG Gly | CCT Pro | TTC Phe | CTA Leu | TGG Trp | TGC Cys (133) | GAA Glu | CAA Gln | AGC Ser |
| 148 | CAA Gln | GGA Gly | TTG Leu | CAG Gln | GAT Asp | AAG Lys | AGA Arg (163) |
| 178 | TGC Cys | CAT His | GGG Gly | CTA Leu | GAC Asp | CAA Gln | CAC His | TGG Trp (193) | GTC Val | GAA Glu | GTC Val |
| 208 | GCC Ala | GTG Val | GAG Glu | CTA Leu |
| 223 | CAA Gln | GAG Glu | TGT Cys | GAC Asp | ATG Met | AGG Arg | ATC Ile (238) | AAC Asn | TGC Cys | AAC Asn | AAG Lys |
| 253 | AAC Asn | CAG Gln | GTG Val | TTC Phe | GAG Glu (268) |
| 283 | GAC Asp | ACG Thr | ATG Met | CCC Pro | CTT Leu | GAG Glu | CAT His (298) | TTC Phe | GAG Glu | TCA Ser | ATG Met | ATG Met |
| 313 | TGC Cys | GAC Asp | ATC Ile | CCA Pro | CTG Leu | CTC Leu |
| 328 | TTG Leu | CTC Leu | CCC Pro | TAC Tyr | AAA Lys | CAA Gln | TGC Cys | CAG Gln (343) | CCC Pro | CGG Arg | CAG Gln |
| 358 | GTG Val | CAG Gln | AAC Asn | TAC Tyr | TTC Phe (373) |
| 388 | GAC Asp | TGC Cys | CCC Pro | ATG Met | TTC Phe | AAC Asn | TCA Ser | ACT Thr (403) | CAG Gln | CCA Pro | GAC Asp | ATC Ile | TGT Cys | GAC Asp | CAC His |
| 418 | GGC Gly | GAG Glu | GAC Asp | CTG Leu | GGG Gly (433) | CTG Leu |
| 448 | TCC Ser | AAA Lys | AAA Lys | CCT Pro | CTG Leu | CCC Pro | CAG Gln | CGG Arg (463) | CCA Pro | GCG Ala | CCA Pro | CCT Pro | GGG Gly | ATG Met |
| 478 | GGG Gly | TAC Tyr | CTG Leu | CTG Leu |
| 493 | CTG Leu | CTG Leu | CGC Arg | CTG Leu | CAG Gln | CCC Pro (508) | CGG Arg |
| 523 | GAC Asp | AGG Arg | CCC Pro | CCT Pro | CCT Pro | AAG Lys | TCA Ser | AAG Lys (538) | ACA Thr |
| 553 | GTG Val | AAA Lys | ATG Met | CTC Leu | TGG Trp | GAC Asp | CAC His | CTC Leu (568) |
| 583 | GGG Gly | TGC Cys | TGG Trp | CTA Leu | GCT Ala | GTG Val |
| 598 | GAT Asp | CTC Leu | CTC Leu | TCC Ser | TTC Phe | ATT Ile | ATG Met | CCT Pro | TAT Tyr | CAC His (613) | CAA Gln | AAG Lys | CAC His | CTC Leu (643) |
| 658 | ATC Ile | AAG Lys | CGG Arg | ATC Ile | ATG Met | GCC Ala (673) | CAA Gln | ATC Ile | CCC Pro | TGG Trp | CTA Leu | TGC Cys | GTG Val | GCT Ala | AGG Arg (703) |
| | ATC Ile | AAG Lys | CAA Gln | GGT Gly (688) |
| 703 | GCA Ala |

TABLE 6-continued

DNA and Corresponding Protein Sequence of 6K Clone

|  |  |  |  |  | | 718 |  |  |  |  |  | 733 |  |  |  | 748 |  |  |  |
|---|---|---|---|---|---|---|---|---|---|---|---|---|---|---|---|---|---|---|---|
| CTG | GTG | CAG | GCC | GTG | CGC | TGC | GTG | CCT | GTA | ATC | GGC | CTG | GTG | GCG | GGC | ATC | TGC | CAG | TGC |
| Leu | Val | Gln | Ala | Val | Arg | Cys | Val | Pro | Val | Ile | Gly | Leu | Val | Ala | Gly | Ile | Cys | Gln | Cys |
|  | 763 |  |  |  |  |  | 778 |  |  |  |  |  | 793 |  |  |  |  | 808 |  |
| CCC | GCT | GAG | CTG | CGC | TCC | TAC | GTC | CTC | GTA | ATC | GGC | CTC | ACG | CTG | CTG | GGC | CGC | ATG | CTG |
| Pro | Ala | Glu | Leu | Arg | Ser | Tyr | Val | Leu | Val | Ile | Gly | Leu | Thr | Leu | Leu | Gly | Arg | MET | Leu |
|  |  | 823 |  |  |  |  |  | 838 |  |  |  | 853 |  |  |  |  |  |  |  |
| CCC | CAG | GTC | TGC | CGC | CGC | CTC | GTC | CTC | CGG | TCC | GTC | GAT | CTG | ATG | AGC | GAC | GCT | CTC | GGC |
| Pro | Gln | Val | Cys | Arg | Arg | Leu | Val | Leu | Arg | Ser | Val | Asp | Leu | MET | Ser | Asp | Ala | Leu | Gly |
| 868 |  |  |  |  |  | 883 |  |  |  |  |  | 898 |  |  |  |  | 913 |  |  |
| CCA | AGG | TCG | CCG | ACA | GGA | GGA | CAG | GAA | TGG | GGG | CCG | CGA | TCC | GAC | TCT | AGC | CAC | CCA | TGC |
| Pro | Arg | Ser | Pro | Thr | Gly | Gly | Gln | Glu | Trp | Gly | Pro | Arg | Ser | Asp | Ser | Ser | His | Pro | Cys |
|  | 928 |  |  |  |  |  | 943 |  |  |  |  | 958 |  |  |  |  |  | 973 |  |
| ATG | GTG | ACC | CAG | CAC | ACC | CAG | GGG | TCC | AAC | CTG | GAC | CAG | GAG | GAG | AGC | ATA | TGC | GCA | CCC |
| MET | Val | Thr | Gln | His | Thr | Gln | Gly | Ser | Asn | Leu | Asp | Gln | Glu | Glu | Ser | Ile | Cys | Ala | Pro |
|  |  | 988 |  |  |  |  |  | 1003 |  |  |  | 1018 |  |  |  |  |  |  |  |
| ATG | CTC | TGT | GTT | GGC | TCC | ACG | CAG | CGA | AGC | CTG | AGG | TGC | GGG | GAA | AAG | AGG | CCC | CAA | TTT |
| MET | Leu | Cys | Val | Gly | Ser | Thr | Gln | Arg | Ser | Leu | Arg | Cys | Gly | Glu | Lys | Arg | Pro | Gln | Phe |
|  | 1033 |  |  |  |  |  |  |  |  |  |  | 1063 |  |  |  | 1078 |  |  |  |
| GTG | GAG | CTC | ACG | ACC | CAG | CCC | GCC | GCC | CTG | CTG | GAC | GTG | AGG | CCC | TGG | GAT | CAG | CTC | GCC |
| Val | Glu | Leu | Thr | Thr | Gln | Pro | Ala | Ala | Leu | Leu | Asp | Val | Arg | Pro | Trp | Asp | Gln | Leu | Ala |
|  |  |  |  |  |  |  |  | 1108 |  |  |  | 1123 |  |  |  |  |  |  |  |
| CAC | ACC | CAC | CAG | AGC | CCC | CTT | CTG | GTG | GGG | CTG | ACC | TCC | AGC | ATG | CCT | ATG | CTC | CAG | GCC |
| His | Thr | His | Gln | Ser | Pro | Leu | Leu | Val | Gly | Leu | Thr | Ser | Ser | MET | Pro | MET | Leu | Gln | Ala |
| 1138 |  |  |  | 1153 |  |  |  | 1166 |  |  | 1176 |  | 1186 |  | 1196 |  |  |  |  |
| TGT | ATC | CAC | AGC | GAC | CTT | TGG | GTG | TGATGAGAAC | | TCAGCTGTCC | | AGCTGCAAAG | | GAAAAGCCAA | | | | |
| Cys | Ile | His | Ser | Asp | Leu | Trp | Val |  |  |  |  |  |  |  |  |  |  |  |  |
| 1206 | | | | 1216 | | | | 1226 | | | | 1236 | | | | 1246 | | | | 1256 | | | | 1266 |
| GTGAGACGGG | | CTCTGGGACC | | ATGGTGACCA | | GGCTCTTCCC | | CTGCTCCCTG | | GCCCTCGCCA | | GCTGCCAGGC |
| 1276 | | | | 1286 | | | | 1296 | | | | 1306 | | | | 1316 | | | | 1326 | | | | 1336 |
| TGAAAAGAAG | | CCTCAGCTCC | | CACACCGCCC | | TCCTCACCTC | | CCTTCCTCGG | | CAGTCACTTC | | CACTGTGGA |
| 1346 | | | | 1356 | | | | 1366 | | | | 1376 | | | | 1386 | | | | 1396 | | | | 1406 |
| CCACGGGCCC | | CCAGCCCTGT | | GTCGGCCTTG | | TCTGTCTCAG | | CTCAACCACA | | GTCTGACACC | | AGAGCCCACT |
| 1416 | | | | 1426 | | | | 1436 | | | | 1446 | | | | 1456 | | | | 1466 | | | | 1476 |
| TCCATCCTCT | | CTGGTGTGAG | | GCACAGCGAG | | GGCAGCATCT | | GGAGGAGCTC | | TGCAGCCTCC | | ACACCTACCA |
| 1486 | | | | 1496 | | | | 1506 | | | | 1516 | | | | 1526 | | | | 1536 | | | | 1546 |
| CGACCTCCCA | | GGGCTGGGCT | | CAGGAAAAAC | | CAGCCACTGC | | TTTACAGGAC | | AGGGGGTTGA | | AGCTGAGCCC |

TABLE 6-continued
DNA and Corresponding Protein Sequence of 6K Clone

| 1556 | 1566 | 1576 | 1586 | 1596 | 1606 | 1616 |
|---|---|---|---|---|---|---|
| CGCCTCACAC | CCACCCCCAT | GCACTCAAAG | ATTGGATTTT | ACAGCTACTT | GCAATTCAAA | ATTCAGAAGA |
| 1626 | 1636 | 1646 | 1656 | 1666 | 1676 | 1686 |
| ATAAAAATG | GGAACATACA | GAACTCTAAA | AGATAGACAT | CAGAAATTGT | TAAGTTAAGC | TTTTTCAAAA |
| 1696 | 1706 | 1716 | 1726 | 1736 | 1746 | 1756 |
| AATCAGCAAT | TCCCCAGCGT | AGTCAAGGGT | GGACACTGCA | CGCTCTGGCA | TGATGGGATG | GCGACCGGGC |
| 1766 | 1776 | 1786 | 1796 | 1806 | 1816 | 1826 |
| AAGCTTTCTT | CCTCGAGATG | CTCTGCTGCT | TGAGAGCTAT | TGCTTTGTTA | AGATATAAAA | AGGGTTTCT |
| 1836 | 1846 | 1856 | 1866 | 1876 | 1886 | 1896 |
| TTTTGTCTTT | CTGTAAGGTG | GACTTCCAGC | TTTTGATTGA | AAGTCCTAGG | GTGATTCTAT | TTCTGCTGTG |
| 1906 | 1916 | 1926 | 1936 | 1946 | 1956 | 1966 |
| ATTTATCTGC | TGAAAGCTCA | GCTGGGGTTG | TGCAAGCTAG | GGACCCATTC | CTGTGTAATA | CAATGTCTGC |
| 1976 | 1986 | 1996 | 2006 | 2016 | 2026 | |
| ACCAATGCTA | ATAAAGTCCT | ATTCTCTTTT | AAAAAAAAAA | AAAAAAAAAA | AACGGAATTC | |

Deduced protein sequence of 6Kd PSP protein is underlined composition of the latter 6 kd protein is set forth in Table 4.

The two approximately 6 kd proteins differ significantly from each other with respect to amino acid composition, as well as from the protein described by Tanaka, Chem. Pharm. Bull. 311:4100 (1983). Additionally, the N-terminal peptide sequence of the cold butanol-insoluble 6 kd protein was determined (Table 5). For the sake of simplicity, both low molecular weight PSP proteins are referred to hereinafter as "6k" proteins based on their approximate apparent molecular weights as determined by conventional SDS-PAGE. It should be understood, however, that the actual molecular weights of these proteins are in the range of 5.5-9 kilodaltons.

The fact that the four proteins can now be obtained in pure form by the above-described methods now makes it possible for one to apply conventional methods to elucidate the amino acid composition and sequence of the proteins; to prepare oligonucleotide probes based on the elucidated peptide sequences; to identify genomic DNA or cDNA encoding the proteins by conventional means, e.g., via (a) hybridization of labeled oligonucleotide probes to DNA of an appropriate library (Jacobs et al., 1985), (b) expression cloning (Wong et al., 1985) and screening for surfactant enhancing activity or (c) immunoreactivity of the expressed protein with antibodies to the proteins or fragments thereof; and to produce corresponding recombinant proteins using the identified genomic DNA or cDNA and conventional expression technology i.e. by culturing genetically engineered host cells such as microbial, insect or mammalian host cells containing the DNA so identified, for instance, transformed with the DNA or with an expression vector containing the DNA.

By way of example, tryptic fragment of one of the two 35 kd proteins were prepared and sequenced. Oligonucleotide probes were synthesized based on the elucidated peptide sequence of the tryptic fragments and were used to screen a lambda gt10 cDNA library made from human lung mRNA. Numerous clones were identified which hybridized to the probes. DNAs from two of these positive clones (PSAP-1 and PSAP-2) were subcloned into M13 for DNA sequencing, thus generating the clones MPSAP-1A and MPSAP-6A. The nucleotide sequence for the cDNA clones encoding each of the two 35 kd surfactant proteins was thereby elucidated and is presented above in Tables 1 and 2, respectively. The sequences of subclones encoding the two 35 kd proteins are similar to each other but not identical. The sequence differences result in restriction fragment polymorphism between the two clones with respect to the coding region recognized by the restriction enzyme PstI. Considerably more nucleotide variation between the two clones was found in their 3' untranslated regions. Plasmids PSP35K-1A-10 and PSP35K-6A-8 were constructed by inserting the approximately 940-950 nucleotide EcoRI fragments depicted in Tables 1 and 2, respectively, into the EcoRI site of plasmid SP65 (see infra). PSP35K-1A-10 contains the polylinker site adjacent to the EcoRI site at cDNA position 1, while PSP35K-6A-8 contains the polylinker site adjacent to the EcoRI site at cDNA position 947. PSP35K-1A-10 and PSP35K-6A-8 have been deposited with the American Type Culture Collection (ATCC), Rockville, Md. under accession Nos. ATCC 40243 and 40244, respectively.

Additionally, oligonucleotide probes based on the N-terminal sequence of the cold butanol-insoluble 6K protein (See Table 5) were synthesized and were used to screen a cDNA library prepared from human lung mRNA (Toole et al., 1984) as described in greater detail in Example 4, below. Several clones which hybridized to the probes were identified.

Based on hybridization intensity one clone was selected, subcloned into M13 and sequenced. Plasmid PSP6K-17-3 was constructed by inserting the cloned cDNA so identified as an EcoRI fragment into the EcoRI site of plasmid SP65 (D.A. Melton et al., 1984, Nucleic Acids Res., 12:7035-7056). PSP6K-17-3 has been deposited with the ATCC under accession No. ATCC 40245. The nucleotide sequence of the cloned cDNA insert is shown in Table 6.

TABLE 5

| 1 | | | | | 5 | | | | 10 | | | |
|---|---|---|---|---|---|---|---|---|---|---|---|---|
| F | P | I | P | L | P | Y | (—) | W | L | (—) | (—) | A | L |

(—) = Not determined
positions 8, 11 and 12 were unidentified

As those skilled in the art will appreciate, the cDNA insert in PSP6K-17-3 contains an open reading frame encoding a protein having a molecular weight of over 40 kd. It is presently believed that the primary translation product is further processed, e.g., by Type II pneumocytes (Alveolar Type II cells), to yield the approximately 6K protein. It is contemplated that the cloned cDNA, portions thereof or sequences capable of hybridizing thereto may be expressed in host cells or cell lines by conventional expression methods to produce "recombinant" proteins having surfactant or surfactant enhancing activity.

With respect to the cloned approximately 6K protein, this invention encompasses vectors containing a heterologous DNA sequence encoding the characteristic peptide sequence Ile through Cys corresponding to nucleotides A-656 through C-757 of the seqence shown in Table 6, i.e., IKRIQAMIPKGALAVAVAQVCRVVPLVAGGICQC. One such vector contains the nucleotide sequence

| ATC | AAG | CGG | ATC | CAA | GCC | ATG | ATT | | |
| CCC | AAG | GGT | GCG | CTA | GCT | GTG | GCA | | |
| GTG | GCC | CAG | GTG | TGC | CGC | GTG | GTA | | |
| CCT | CTG | GTG | GCG | GGC | GGC | ATC | TGC | CAG | TGC |

Other vectors of this invention contain a heterologous DNA sequence encoding the characteristic peptide sequence substantially as depicted in the underlined peptide region of Table 6, i.e., FPIPLPYCWL-CRALIKRIQAMIPKGALAVAVAQVCRVVP-LVAGGICQCLAERYSVILLDTLLGRML. One such vector contains the DNA sequence substantially as depicted in the underlined nucleotide sequence of Table 6, i.e.,

| TTC | CCC | ATT | CCT | CTC | CCC | TAT | TGC | TGG | CTC | TGC | AGG | GCT | CTG | |
|-----|-----|-----|-----|-----|-----|-----|-----|-----|-----|-----|-----|-----|-----|-----|
| ATC | AAG | CGG | ATC | CAA | GCC | ATG | ATT | CCC | AAG | GGT | GCG | CTA | GCT | GTG |
| GCA | GTG | GCC | CAG | GTG | TGC | CGC | GTG | GTA | CCT | CTG | GTG | GCG | GGC | GGC |
| ATC | TGC | CAG | TGC | CTG | GCT | GAG | CGC | TAC | TCC | GTC | ATC | CTG | CTC | GAC |
| ACG | CTG | CTG | GGC | ATG | CTG | | | | | | | | | |

Another exemplary vector contains a heterologous DNA sequence, such as the nucleotide sequence depicted in Table 6, which encodes the full-length peptide sequence of Table 6. DNA inserts for such vectors which comprise a DNA sequence shorter than the full-length cDNA of PSP6K-17-3, depicted in Table 6, may be synthesized by known methods, e.g. using an automated DNA synthesizer, or may be prepared from the full-length cDNA sequence by conventional methods such as loop-out mutagenesis or cleavage with restriction enzymes and ligation. Vectors so prepared may be used to express the subject proteins by conventional means or may be used in the assembly of vectors with larger cDNA inserts. In the former case the vector will also contain a promoter to which the DNA insert is operatively linked and may additionally contain an amplifiable and/or selectable marker, all as is well known in the art.

The proteins of this invention may thus be produced by recovering and purifying the naturally-occuring proteins from human pulmonary lavage material as described hererin. Alternatively, the corresponding "recombinant" proteins may be produced by expression of the DNA sequence encoding the desired protein by conventional expression methodology using microbial or insect or preferably, mammalian host cells. Suitable vectors as well as methods for inserting therein the desired DNA are well known in the art. Suitable host cells for transfection or transformation by such vectors and expression of the cDNA are also known in the art.

Mammalian cell expression vectors, for example, may be synthesized by techniques well known to those skilled in this art. The components of the vectors such as the bacterial replicons, selection genes, enhancers, promoters, and the like may be obtained from natural sources or synthesized by known procedures. See Kaufman, Proc. Natl. Acad. Sci. 82: 689–693 (1985).

Established cell lines, including transformed cell lines, are suitable as hosts. Normal diploid cells, cell strains derived from in vitro culture of primary tissue, as well as primary explants are also suitable. Candidate cells need not be genotypically deficient in the selection gene so long as the selection gene is dominantly acting.

The host cells preferably will be established mammalian cell lines. For stable integration of vector DNA into chromosomal DNA, and for subsequenct amplification of integrated vector DNA, both by conventional methods, CHO (Chinese hamster Ovary) cells are generally preferred. Alternatively, the vector DNA may include all or part of the bovine papilloma virus genome (Lusky et al., Cell, 36:391–401 (1984) and be carried in cell lines such as C127 mouse cells as a stable episomal element. Other usable mammalian cell lines include HeLa, COS-1 monkey cells, mouse L-929 cells, 3T3 lines derived from Swiss, Balb-c or NIH mice, BHK or HaK hmaster cell lines and the like. Cell lines derived from Alveolar Type II cells may be preferred in certain cases such as expression of the 6K protein (alone or with one or more other proteins of this invention) using the cDNA insert from PSP6K-13-7 or a fragment thereof.

Stable transformants then are screened for expression of the product by standard immunological or enzymatic assays. The presence of the DNA encoding the proteins may be detected by standard procedures such as Southern blotting. Transient expression of the DNA encoding the proteins during the several days after introduction of the expression vector DNA into suitable host cells such as COS-1 monkey cells is measured without selection by activity or immunological assay of the proteins in the culture medium.

In the case of bacterial expression, the DNA encoding the protein may be further modified to contain preferred codons for bacterial expression as is known in the art and preferably is operatively linked in-frame to a nucleotide sequence encoding a secretory leader polypeptide permitting bacterial secretion of the mature variant protein, also as is known in the art. The compounds expressed in mammalian, insect or microbial host cells may then be recovered, purified, and/or characterized with respect to physicochemical, biochemical and/or clinical parameters, all by known methods.

One or more of the proteins of this invention may be combined with a pharmaceutically acceptable fatty acid or lipid such as dipalmitoylphosphatidyl choline or with mixtures of such fatty acids of lipids which may be obtained from commercial sources or by conventional methods, or with natural surfactant lipids to provide a formulated pulmonary surfactant composition. Natural surfactant lipids may be extracted by known methods from lung lavage, e.g. bovine or human lung lavage. Typically the weight ratios of total lipids to total proteins in the composition will be about 20:1 to about 100:1. At the levels currently being tested in clinical trials, one dose of the surfactant composition corresponds to 1–2 mg of total protein and 98–99 mg. of total lipid.

It is contemplated that certain subcombinations of (1) the 35 kd protein encoded for by the nucleotide sequence of Table 1, (2) the 35 kd protein encoded for by the nucleotide sequence of Table 2, (3) the 6 kd protein encoded by the cDNA sequence of Table 6 and having the amino acid composition set forth in Table 3 and (4) the 6 kd protein having the amino acid composition set forth in Table 4 may be especially useful in the treatment of patients with particular clinical indications. Thus, this invention specifically contemplates the following subcombinations and compositions containing such subcombinations:

At present compositions containing proteins (3) and/or (4) are preferred.

EXPERIMENTAL EXAMPLES

EXAMPLE 1

Isolation and Characterization of the 35 kd Surfactant Associated Proteins

Pulmonary lavage (50 ml) from an alveolar proteinosis patient was centrifuged at 10,000 ×g for 5 min. The pellet was collected and washed 5 times in 20 mm Tris HCl, 0.5 M NaCl, pH 7.4. The lipids and lipidassociated proteins were extracted from the washed pellet by shaking with 50 ml 1-butanol for 1 hr at room temperature. The butanol-insoluble material was collected by centrifugation, washed with distilled water and dissolved in 50 mM sodium phosphate, pH 6.0 and 6M guanidine HCl. The protein was applied to a Vydac C4 reverse phase column and eluted with a gradient of acetonitrile: 2-propanol (2:1,v:v) containing 0.1% trifluoroacetic acid. The major protein peak eluting at 50% B was collected and evaporated to dryness. The proteins present were analyzed by SDS-PAGE (Laemmli, 1970).

Alkylation and Tryptic Mapping

The protein so obtained (approx. 50 ug) was taken up and reduced in 200 mM Tris, 1 mM EDTA, 6M guanidine HCl, 20 mM DTT, pH8.5 at 37° C. for 2 hrs. Solid iodacetamide was added to a final concentration of 60 mM and the reaction incubated at 0° C. for 2 hrs under argon in the dark. The reaction was stopped and the reagents removed by dialysis into 0.1M $NH_4HCO_3$, 50 mM 2-mercaptoethanol, pH7.5 followed by further dialysis into 100 mM $NH_4HCO_3$, pH7.5. The alkylated protein was digested with trypsin (3% trypsin by weight) at 37° C. for 16 hrs and the digest chromatographed over a C18 Vydac Reverse phase HPLC column (4.6×250 mm).

The tryptic peptides were eluted with a linear gradient of 95% acetonitrile and 0.1% TFA, collected and subjected to N-terminal Edman degradation using an Applied-Biosystems Model 470A protein sequencer. The PTH-amino acids were analyzed by the method of Hunkapillar and Hood (1983). Sequence data so obtained for tryptic fragments T19, T26 and T28 is presented below in Table 7.

EXAMPLE 2

Isolation and Characterization of the Low Molecular Weight Lipid Associated Proteins The butanol extract obtained in Example 1 was stored at −20° C. causing precipitation of one of the low MW proteins. The precipitate was collected by centrifugation and dried under vacuum. The butanol layer containing butanol-soluble protein was evaporated to dryness. The precipitated cold butanol insoluble protein and the cold butanol-soluble protein were then purified in parallel by the same method as follows. Each crude protein was separately dissolved in $CHCl_3$: MeOH (2:1, v/v), applied to Sephadex LH20 columns and eluted with $CHCl_3$:MeOH (2:1). The proteins were then analyzed by SDS-PAGE. Fractions containing the protein were pooled and evaporated to dryness. Amino acid composition was determined by hydrolysis in 6 N HCl at 110° C. for 22 hrs followed by chromatography on a Beckman model 63000 amino acid analyzer. N-terminal sequence was determined on an Applied Biosystems 470A sequencer. Molecular weights were determined on 10–20% gradient SDS polyacrylamide gels.

TABLE 7

| Peptide | Observed Sequence |
|---|---|
| T19 | Asp Val Cys Val Gly Ser Hyp Gly Ile Hyp Gly Thr Hyp Gly Ser His Gly Leu Pro Gly |
| T26 | Ala Leu Ser Leu Gln Gly Ser Ile MET Thr Val (−) (−) Lys |
| T28 | Asn Pro Glu Glu Asn Glu Ala Ile |

TABLE 7-continued

| Peptide | Observed Sequence |
|---|---|
| | Ala (−) Phe Val Lys |

"Hyp" = hydroxyproline

EXAMPLE 3

Screening of the cDNA Library and Sequencing of Clones for the 35 Kd Proteins Based on the amino acid sequence of tryptic fragment T28, (Table 7) an oligonucleotide probe was synthesized. The probe consisted of four pools of 20 mers and each pool contained 32 different sequences. The sequences of the 20 mers are depicted in Table 8.

A cDNA library from human lung mRNA was prepared as described in Toole et al., (1984) and screened with the total mixture of the four pools using tetramethyl ammoniumchloride as a hybridization solvent (Jacobs et al., 1985) Between 0.5–1% of the phage clones were positive with this probe.

DNA from two of these clones were subcloned into M13 for DNA sequence analysis. By using Pool II as a sequencing primer, the nucleotide sequence corresponding to tryptic fragment T26 was identified in both clones, confirming that the isolated clones code for the major protein species found in the partially purified 35 kd protein from lavage material of alveolar proteinosis patients (see above).

The two clones differed in nucleotide sequence at three positions out of 250 nucleotides. Both clones were completely sequenced by generating an ordered set of deletions with Bal 31 nuclease, recloning into other M13 vectors and sequencing via the dideoxynucletide chain termination procedure (Viera and Messing, 1982; Sanger et al., 1977). One clone corresponded to a full-lenth copy of the type referred to as 1A (Table 1), the second to an incomplete copy of the type referred to as 6A (Table 2). By using an oligonucleotide specific for type 6A, a full-length clone of this type was identified. The 5' EcoRI fragment of the

TABLE 8

Four 20-mer Oligonucleotide Pools For Cloning 35K PSP Proteins

T  A             A
GCCTCGTTTTCTTCNGGGTT

T  A             A
GCCTCGTTTTCCTCNGGGTT

T  A             A
GCCTCGTTCTCTTCNGGGTT

T  A             A
GCCTCGTTCTCCTCNGGGTT lambda gt10 cDNA clone was subcloned into M13 and sequenced as above by using specific olignucleotides as primers. This sequence is presented in Table 2. The two clones differ within the coding region at 7 nucleotides which led to amino acid changes and at 6 nucleotides which resulted in silent changes. These changes result in restriction fragment polymorphism between the two clones within the coding region for the restriction enzyme PstI. Clone 6A has 2 PstI sites at the nucleotide position 454 and 478 (Table 2) and clone 1A has 3 PstI sites at 454, 478 and 756 (Table 1). Additional DNA sequencing of each clone at the 3' untranslated region revealed a large 1kb untranslated region and considerably more nucleotide variation between MPSAP-1A and MPSAP-6A.

DNA Binding and Hybrid Selection

Very dilute (10–15 ug/ml) single stranded DNA from either subclone MPSAP-1A or MPSAP-1B was applied to nitrocellulose paper (10 ug/cm) under vacuum (Kafatos et al., 1979). MPSAP-1A represents the M13 subclone of a 0.9 kb ECOR1 fragment in one orientation in M13. MPSAP-1B represents the same fragment cloned in the opposite orientation in M13. Each filter (1 cm$^2$) was cut into nine equal size pieces and each piece was used in a 20-30 ul hybridization reaction. Each reaction contained human lung RNA (5 mg/ml), 50% deionized formamide (Fluka AG Chemical Corp.), 10 mM PIPES [(Piperazine-N, N'-bis) (2-ethanesulfonic acid)]pH 6.4 and 0.4M NaCl (Miller et al., 1983). The source and preparation of the RNA have been reported previously (Floros et al., 1985). Each hybridization reaction was routinely incubated at 50° C. for 3 hrs. At the end of the incubation period each filter was washed for five minutes with 1 ml LXSSC (0.15M NaCl, 0.015M sodium citrate, 0.5% SDS at 60° C. five times. Then it was washed for five minutes with 1 ml of 2 mM EDTA, pH 7.9 at 60° C. three times. The selected RNA was eluted by boiling for one minute in 300 ul of 1 mM EDTA pH 7.9 and 10 ug of yeast tRNA (Boehringer, Mannheim). The precipitated RNA was translated, immunoprecipitated and subjected to one and two dimensional gel electrophoresis as described in Floros et al., 1985.

EXAMPLE 4

Screening of the cDNA Library and Sequencing of Clones for the 6 Kd Proteins Based on the first six amino acids of the sequence shown in Table 5 an oligonucleotide probe was synthesized. The probe consisted of six pools of 17 mers. Three of the pools each contained 128 different sequences, and three of the pools each contained 64 different sequences. Based on the first seven amino acids two pools of 20 mers were synthesized. These pools contained either 384 or 192 different sequences.

A cDNA library from human lung mRNA was prepared as described in Toole et al., (1984) and screened with the total mixture of the six pools using tetramethylammoniumchloride as a hybridization solvent (Jacobs et al., 1985). Approximately 100,000 phage were screened, and 100 phage which hybridized to the probe were plaque purified. The phage were then pooled into groups of 25 and screened with the individual 17 mer and 20 mer pools. Six phage which hybridized most intensely to one of the 20 mer oligonucleotide probes and one of the corresponding 17 mer pools (pool 1447 containing 128 different sequences) were plaque purified. The 17 mer pool 1447 was divided into four pools of 32 different sequences and hybridized to a dot blot of DNA prepared from these phage.

Based on the hybridization intensity, DNA from one of these six phage were subcloned into M13 and DNA sequence analysis. A sequence corresponding in identity and position to the amino acids shown in Table 5 was obtained, confirming that the isolated clone coded for the approximately 6kd cold butanol-insoluble protein found in the lavage material of alveolar proteinosis patients (see above).

The first clone obtained was presumed to be an incomplete copy of the mRNA because it lacked an initiating methionine, and was used to isolate longer clones. Two clones were completely sequenced by generating an ordered set of deletions with Bal 31 nuclease, recloning into other M13 vectors and sequencing via the dideoxynucleotide chain termination procedure (Viera and Messing, 1982; Sanger et al., 1977). One clone corresponded to a full-length copy of the type referred to as 17 (Table 6), the second began at nucleotide 148 of clone 17. Sequence of the 5' end of a third clone confirmed the sequence of the 5' end of clone 17. The clones are identical throughout the coding region and differ only at two positions in the 3' untranslated region.

| REFERENCES |
| --- |
| 1. Bhattacharyya, S. N., and Lynn, W. S. (1978) Biochem. Biophys. Acta 537, 329–335 |
| 2. Bhattacharyya, S. N., and Lynn, W. S. (1980) Biochem. Biophys. Acta 625, 451–458 |
| 3. Bhattacharyya, S. N., Passero, M. A., DiAugustine, R. P., and Lynn, W. S. (1975) J. Clin. Invest. 55, 914–920 |
| 4. Floros, J., Phelps, D. S., and Taeusch, W. H. (1985) J. Biol. Chem. 260, 495–500 |
| 5. Hawgood, S., Benson, B. J., and Hamilton, Jr. R. L. (1985) Biochemistry 24, 184–190 |
| 6. Hunkapiller, M. W. and Hood, L. E. (1983) Methods in Enzymology 91, 486– |
| 7. Jacobs, K., Shoemaker, C., Rudersdorf, R., Neil, S. D., Kaufman, R. J., Mufson, A., Seehra, J., Jones, S. S., Hewick, R., Fritsch, E. E., Kawakita, M., Shimizu, T., and Miyake, T. (1985) Nature (Lond.) 313, 806–810. |
| 8. Kafatos, E., Jones, W. C., and Efstratiadis, A. (1979) Nucleic acid Rest. 7, 1541–1552. |
| 9. Katyal, S. L., Amenta, J. S., Singh, G., and Silverman, J. A. (1984) Am. J. Obstet. Gynecol. 148, 48–53. |
| 10. Katyal, S. L. and Singh, G. (1981) Biochem. Biophys. Acta 670, 323–331. |
| 11. King, R. J., Carmichael, M. C., and Horowitz, P. M. (1983) J. Biol. Chem. 258, 10672–10680. |
| 12. King, R. J. (1982) J. Appl. Physiol. Exercise Physiol. 53, 1–8. |
| 13. King, R. J., Klass, D. J., Gikas, E. G., and Clements, J. A. (1973) Am. J. Physiol. 224; 788–795. |
| 14. King, R. J., Ruch, J., Gikas, E. G., Platzker, A. C. G., and Creasy, R. K. (1975) J. of Applied Phys. 39, 735–741. |
| 15. Laemmli, U. K. (1970) Nature (Lond.) 227, 680–685. |
| 16. Miller, J. S., Paterson, B. M., Ricciardi, R. P., Cohen, L and Roberts, B. E. (1983) Methods in Enzymology 101p. 650–674. |
| 17. Phelps, D. S., Taeusch, W. H., Benson, B., and Hawgood, S. (1984) Biochem. Biophs. Acta, 791–226–238. |
| 18. Shelley, S. A., Balis, J. U., Paciga, J. E., Knuppel, R. A., Ruffolo, E. H., and Bouis, P. J. (1982) Am. J. Obstet. Gynecol. 144, 224–228. |
| 19. Sigrist, H., Sigrist-Nelson, K., and Gither, G. (1977) BBRC 74, 178, 184. |
| 20. Sueishi, K., and Benson, G. J. (1981) Biochem. Biophys. Acta 665, 442–453. |
| 21. Toole, J. J., Knopf, J. L., Wozney, J. M., Sultzman L. A., Bucker, J. L., Pittman, D. D., Kaufman, R. J., Brown, E., Shoemaker, C., Orr, E. C., Amphlett, G. W., Foster, W. G., Coe, M. L., Knutson, G. L., Eass, D. N., Hewick, R. M. (1984) Nature (Lond.) 312, 342–347. |
| 22. Whitsett, J. A., Hull, W., Ross, G., and Weaver, T. (1985) Pediatric Res. 19, 501–508. |
| 23. Wong, G. G. et al., 1985, Science, 228:810-815 |

What is claimed is:

1. A purified human protein useful for enhancing pulmonary surfactant activity characterized by a molecular weight of about 35,000 daltons and a polypeptide sequence encoded by a DNA sequence selected from the group consisting of the cDNA insert in vector PSP35K-1A-10 (ATCC No. 40243) and the cDNA insert in vector PSP35K-68-A (ATCC No. 40244).

* * * * *